United States Patent [19]

Bruner, Jr. et al.

[11] Patent Number: 5,710,325

[45] Date of Patent: Jan. 20, 1998

[54] MANUFACTURE OF ADIPIC ACID

[75] Inventors: Harold Stanley Bruner, Jr., Hockessin, Del.; Samuel Livingston Lane; Bruce Edwin Murphree, both of Beaumont, Tex.

[73] Assignees: E. I. Du Pont de Nemours and Company, Wilmington, Del.; DSM, N.V., Galeen, Netherlands

[21] Appl. No.: 740,812

[22] Filed: Nov. 1, 1996

[51] Int. Cl.$^6$ .................... C07C 51/10; C07C 51/14; C07C 55/14

[52] U.S. Cl. .................... 562/517; 562/590

[58] Field of Search .................... 562/517, 590

[56] References Cited

U.S. PATENT DOCUMENTS

| | | | |
|---|---|---|---|
| 4,788,333 | 11/1988 | Burke | 562/517 |
| 4,788,334 | 11/1988 | Burke | 562/591 |
| 4,939,298 | 7/1990 | Burke | 562/591 |
| 5,218,144 | 6/1993 | Atadan | 562/517 |
| 5,227,522 | 7/1993 | Denis et al. | 562/522 |
| 5,292,944 | 3/1994 | Atadan, et al. | 562/590 |

FOREIGN PATENT DOCUMENTS 0395038  4/1990  European Pat. Off. ........ C07C 55/14

*Primary Examiner*—Gary Geist
*Assistant Examiner*—Rosalynd A. Keys

[57] ABSTRACT

This invention provides a process for the preparation of adipic acid from pentenoic acids or esters of pentenoic acids by hydrocarboxylation of a reaction mixture in which gamma-valerolactone constitutes 30 to 70% by weight of the reaction mixture.

5 Claims, 1 Drawing Sheet

MANUFACTURE OF ADIPIC ACID

FIELD OF THE INVENTION

This invention relates to a process for the manufacture of adipic acid.

BACKGROUND OF THE INVENTION

One method by which adipic acid may be synthesized is by hydrocarboxylation of pentenoic acids and esters. Burke in U.S. Pat. No. 4,788,333 and U.S. Pat. No. 4,788,334 teaches a process for making adipic acid involving the hydrocarboxylation of pentenoic acids and their esters. Pentenoic acids and their esters, in particular 3-pentenoic acid and its esters, are readily available from butadiene and butadiene derived feedstocks by metal catalyzed hydrocarboxylation. Preparation of adipic acid from these feedstocks has the potential of providing a high yield, high rate, low pollution process for the commercial manufacture of adipic acid.

In the hydrocarboxylation of 3-pentenoic acid and its esters (hereinafter referred to as pentenoic acid), undesirably high levels of branched products are formed. Burke (U.S. Pat. No. 4,788,333) taught that, for the production of adipic acid by hydrocarboxylation of pentenoic acid isomers, high linear selectivity is obtained when an iodide promoted rhodium catalyst is employed in conjunction with selected halocarbon solvents. While better linear selectivity is obtained in halocarbon solvents, their use results in additional costs associated with the containment, recovery and recycle of these volatile, environmentally hazardous solvents.

Denis et al. (U.S. Pat. No. 5,227,522) and Atadan (U.S. Pat. No. 5,218,144) taught the use of iodine-promoted iridium catalyst for the hydrocarboxylation of pentenoic acid in a carboxylic acid solvent to produce adipic acid.

Burke taught in U.S. Pat. No. 4,939,298, that branched diacids can be isomerized to adipic acid by heating in the presence of carbon monoxide and an iodide or bromide promoted rhodium catalyst. Atadan and Bruner (U.S. Pat. No. 5,292,944) and Denis et al. (WO 94/21586) taught a process for isomerization of branched diacids to adipic acid under pressure. Atadan and Bruner (U.S. Pat. No. 5,292,944) further taught conversion of branched acids to pentenoic acids at lower pressure (so-called dehydrocarboxylation).

The most commonly used promoters for metal catalyzed hydrocarboxylation also promote the conversion of pentenoic acid isomers to valerolactones. These lactones normally consist primarily of gammavalerolactone (hereinafter referred to as valerolactone). Valerolactone can be hydrocarboxylated to adipic acid as described in Burke EP-A 0395038 and in Denis et al. EP-A 612711, but there are cost and yield losses associated with such a process.

The prior art also taught the use of halocarbons, organic acids or a mixture of organic acid with alkane or aromatic hydrocarbons as the solvent for the conversion of pentenoic acid to adipic acid. To ensure the optimum yield of adipic acid in these solvents, relatively mild reaction conditions had be used which resulted in rather slow reaction rates. When higher temperature or iodine levels were employed in order to improve reaction rates in any of these prior art processes, yield losses resulted. Yields of adipic acid decreased while yields of valerolactone, increased. Valerolactone is known to require extremely long residence times to react under the prior art reaction conditions making it necessary to react the valerolactone, at reduced yields, in another vessel or to react it at more vigorous conditions. In many cases it was simply purged as a byproduct.

The present invention overcomes the disadvantage and yield losses of the prior art by carrying out the conversion of pentenoic acid to adipic acid in a reaction mixture that is in 30–70% percent by weight valerolactone. Selecting the concentration of valerolactone in the reaction mixture to be within this range of weight percents allows the present process to benefit from the rapidly established thermal equilibrium of the reaction which converts pentenoic acid to valerolactone. Once the concentration ratio of valerolactone to pentenoic acid is approximately 50:1, pentenoic acid reacts to yield adipic acid without additional formation of valerolactone; the conversion of pentenoic acid to valerolactone being precluded by the established equilibrium.

Maintaining the concentration of valerolactone within the range of 30–70% by weight of the reaction mixture ensures that the concentration of pentenoic acid in the reaction mixture can be maintained at concentrations producing a reasonable reaction rate for commercial purposes while eliminating the yield losses to valerolactone. Furthermore, the reduced viscosity of the reaction mixture of the present invention produces larger crude crystals of adipic acid which are more easily filtered from the reaction mixture. These crude crystals also have greater purity that those produced by the prior art processes.

SUMMARY OF THE INVENTION

A process for the preparation of adipic acid from pentenoic acid or mixtures of pentenoic acid isomers which comprises:

(a) forming a reaction mixture containing the pentenoic acids or mixtures thereof, water, carbon monoxide, gamma-valerolactone, an iridium catalyst promoted with bromide or iodide and optionally a strong acid reaction promoter wherein the concentration of gamma-valerolactone is from 30 to 70% by weight of the reaction mixture; and (b) reacting the mixture to convert pentenoic acids or esters to adipic acid and branched six carbon dicarboxylic isomers of adipic acid.

A strong acid reaction promoter may be used in the process of the present invention. The preferred acid promoter is selected from the group consisting of triflic, p-toluenesulfonic and phosphoric acid.

The process of the present invention may be operated as a batch or a continuous process. As a continuous process, it is preferred to add subsequent to step (b) the steps:

(c) removing a portion of the mixture as a product stream and recovering crude adipic acid and forming a by-product stream;

(d) subjecting the by-product stream to dehydrocarboxylation to convert a part of the by-product branched six carbon dicarboxylic isomers of adipic acid to pentenoic acid isomers forming a recycle stream; and (e) combining the recycle stream and fresh feed to form the reaction mixture of step (a).

The crude crystals of adipic acid recovered from the product stream of the present process are larger in size, easier to separate from the product stream and of higher purity than those produced by prior art processes.

BRIEF DESCRIPTION OF THE DRAWING

The drawing is a representation of a continuous process according to the present invention.

DETAILED DESCRIPTION OF THE INVENTION

Figure 1:
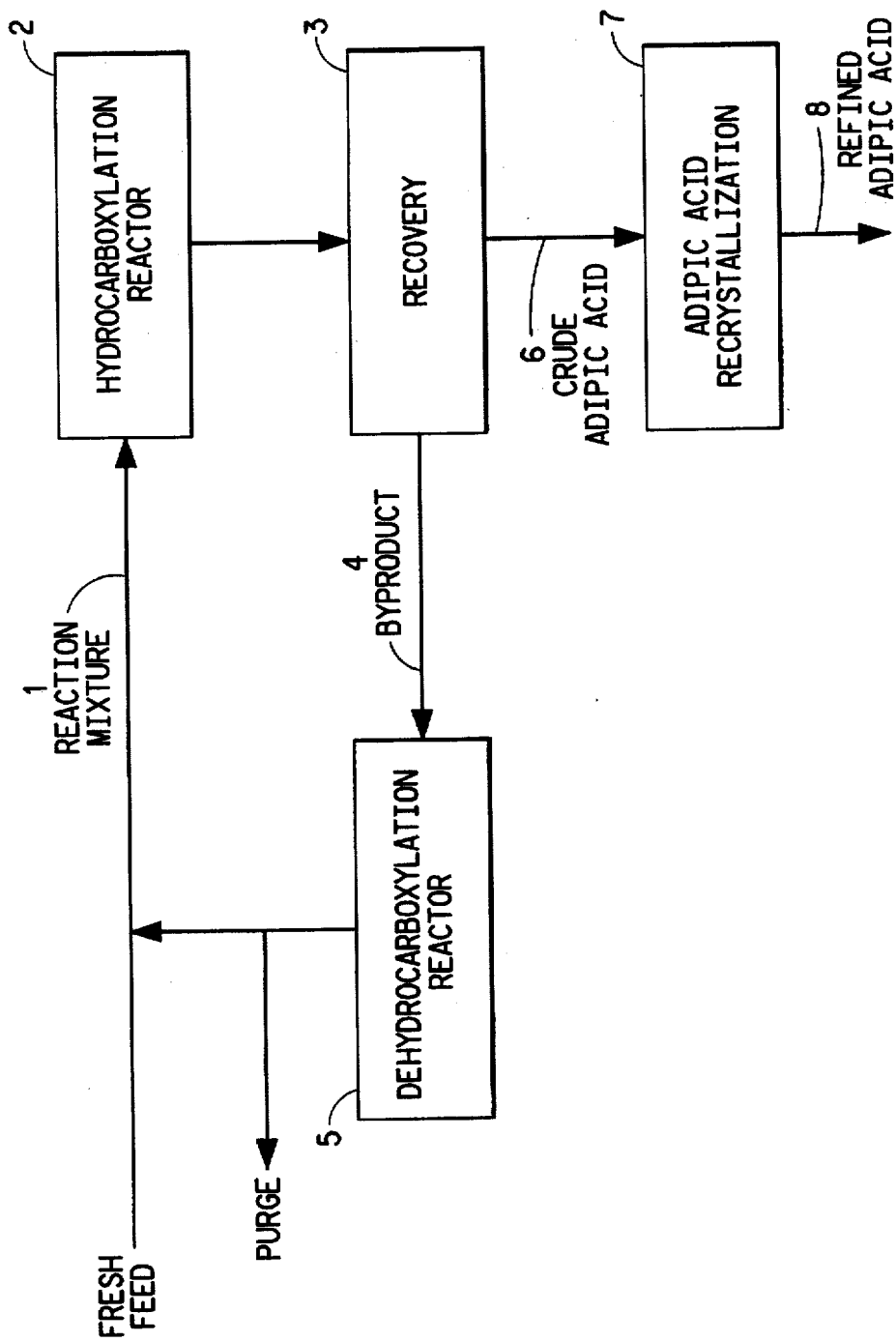

The present invention provides an efficient, low pollution route to adipic acid based on iodide promoted, iridium catalyzed hydrocarboxylation of selected pentenoic acid compounds in a reaction mixture that is from 30 to 70% by weight valerolactone.

A reaction mixture containing pentenoic acids or esters, water, carbon monoxide, valerolactone, an iridium catalyst promoted with bromide or iodide is formed in which the valerolactone, makes up 30 to 70 percent by weight of the reaction mixture. Preferably the weight percent of valerolactone in the reaction mixture is from 50 to 70%. According to the present process, this mixture is reacted to convert pentenoic acid to adipic acid and branched isomers of adipic acid. The branched isomers include, for example, 2-methylglutaric acid and 2-ethylsuccinic acid. Other by-products include valeric acid and 2-methylbutyric acid.

In a batch operation of the present process, after sufficient reaction time the adipic acid formed in the reaction is recovered by crystallization. The low viscosity of the reaction mixture allows the crude adipic acid to crystallize as large, relatively pure crystals.

The present process may also be operated as a continuous process by separating a product stream, crystallizing and separating the product adipic acid from the product stream and processing the various by-products to produce a suitable recycle stream. A representative continuous process is shown in the Figure.

With reference to the Figure, fresh feed is combined with the recycle stream (primarily converted pentenoic acids, recycle catalyst and valerolactone) from the dehydrocarboxylation reactor 5 such that the concentration of valerolactone in the reaction mixture 1 is from 30 to 70% by weight. This mixture is fed into a hydrocarboxylation reactor 2 with the other reactants and additional catalyst and reacted to form crude adipic acid. The crude adipic acid crystals are recovered from the reaction mixture 3 forming a by-product stream 4 (mother liquor from the crystallization) which is fed to a dehydrocarboxylation reactor 5.

The dehydrocarboxylation reaction converts the branched isomers of adipic acid and other by-products to pentenoic acid isomers (including valerolactone). Since the dehydrocarboxylation reactor also may serve the function to distill and separate, a portion of the pentenoic acid isomers may be taken overhead and returned as recycle to the hydrocarboxylation reactor. By-product valeric acid and 2-methylbutyric acid may be converted to butenes and purged. The catalyst in the residual tails may also be recycled to the hydrocarboxylation reactor. It is preferred to run the dehydrocarboxylation reaction as described in U.S. Pat. No. 5,292,944 to Atadan, et al. incorporated herein by reference.

The crude adipic acid recovered 6 may be purified by recrystallization 7 or other methods known in this art.

A surprising feature of the present process is the use of valerolactone as the reaction medium or the solvent for the reaction. The inventors of the present process have found that as the percentage of valerolactone increases in the reaction mixture, the level of pentenoic acid in the reaction also increases to that of the valerolactone/pentenoic acid equilibrium concentration ratio (approximately 50 to 1). By selecting the concentration of valerolactone to be in the range of 30 to 70% by weight of the reaction mixture, the present process ensures that a concentration of pentenoic acid may be present in the reaction mixture such that a high reaction rate to adipic acid results and that the concentration ratio of valerolactone/pentenoic acid is at or near the valerolactone/pentenonic acid equilibrium concentration ratio. In any reaction system other than that of the present invention, the subject reaction proceeds in a way to establish concentrations in keeping with the thermal equilibrium resulting in a significant yield loss to the formation of valerolactone from the reactant pentenoic acid. The relationship of the equilibrium concentrations and reaction rate provide the range limits on the concentration of valerolactone that is preferred for the reaction mixture of the present invention. These concentration range limits are from 30 to 70% by weight of the reaction mixture and more preferably from 50 to 70%. A reaction mixture having less than about 30% by weight valerolactone would require either a very high conversion (therefore large and expensive) backmixed reactor and/or a very low pentenoic acid feed rate since the concentration of pentenoic acid is so low that the rate of conversion to adipic acid is very low. On the other hand, the reactivity of valerolactone in the adipic acid synthesis and in dehydrocarboxylation of reaction by-products makes a reaction mixture of greater than 70% by weight valerolactone difficult to achieve.

It is also of interest that other lactone solvents (lactones other than valerolactone) cannot be used in the present process since other lactone are not only reactive under the process conditions to produce undesired products, but they do not enjoy the benefit of participating in the establishing of the valerolactone/pentenoic acid reaction equilibrium.

It is known in the synthesis of adipic acid that the addition of strong acid accelerates both hydrocarboxylation reaction and the reaction of pentenoic acid to valerolactone. In the reaction processes of the prior art, any addition of such an acid reaction rate promoter contributed to yield losses and was generally avoided.

The equilibrium relationship of the valerolactone/pentenoic acid in the present process enables the process use an acid promoter without suffering yield losses. Although the addition of a strong acid promoter is not necessary to realize the advantage of the present process, a strong acid promoter may be used in the present process without negatively effecting the yield of pentenoic acid to adipic acid.

If a strong mineral acid is to be used in the present process, the mineral acid must be a non-oxidizing, strong acid, having a conjugate base that is a poor ligand such as phosphoric acid. Examples of strong organic acid promoters that may be used are triflic acid, p-toluenesulfonic acid. Of these acids phosphoric preferred because of its low cost. HCl, where the chloride is also a good ligand, is ineffective. Strong oxidizing acids, like nitric or sulfuric acid, will destroy the iridium catalyst and should be avoided.

The crystallization of the crude adipic acid from the reaction mixture of the present invention, provides a product of good purity and good handling characteristics. Crude adipic acid crystals recovered from the product mix of the present process are large, easy to filter and have a level of impurities that is more than ten (10) times less than those recovered from prior known processes.

Suitable starting pentenoic acids for the process of this invention include 2-pentenoic acid, 3-pentenoic acid, 4-pentenoic acid and the esters of these carboxylic acids. Examples of esters which can be employed in the process of the present invention include the methyl and ethyl esters. Feedstocks which consist primarily of 3-pentenoic acid or its esters are preferred for reasons of cost and availability. When all or part of the feed is a pentenoic acid monoester, the product may be converted to adipic acid monoester which can be hydrolyzed in situ or in a subsequent step to give adipic acid.

The iridium catalyst can be provided from any source or by any material which will produce iridium ions under hydrocarboxylation conditions, i.e. iridium materials that are soluble in the other components of the reaction mixture. Among the materials which can be employed as the source of iridium are iridium metal, iridium salts, iridium oxides, iridium carbonyl compounds, organoiridium compounds, coordination compounds of iridium and mixtures thereof. Specific examples of such compounds include, but are not limited to, iridium(III) chloride and its hydrates, iridium(III) bromide and its hydrates, iridium(III) iodide, iridium(III) oxide, iridium(IV) oxide, iridium(III) acetylacetonate, iridium(III) nitrate, iridium (III) ethylhexanoate and dodecacarbonyl tetrairidium.

Preferred sources of iridium catalyst include iridium(III) iodide, iridium(III) acetate and iridium(I) dicarbonyl acetylacetonate.

Suitable concentrations of iridium are in the range of about 100 ppm to 5000 ppm (parts per million) based on the weight of the reaction mixture although higher levels may be employed. Preferably, the concentration of iridium is in the range of 400 ppm to 4000 ppm, more preferably 800 ppm to 2000 ppm.

The iridium catalyst, which can be preformed or formed in situ, must be promoted by a source of iodide that is soluble in the other components of the reaction mixture in order to get satisfactory results. Although it is generally preferable to keep the concentration of iodide promoter below about 8,000 ppm total iodide based on the weight of the reaction mixture, the absolute level of iodide is not as critical as the molar ratio of iodide to iridium. Iodide to iridium ratios between 1 and 3 are preferred and ratios between 2 and 3 are most preferred. When iodide to iridium ratios of greater than about 3:1 are employed, it is advantageous to employ lower iridium concentrations. This serves to reduce the total concentration of free hydrogen iodide and thus reduce the overall corrosivity of the reaction mixture.

The iodide promoter can be provided by hydrogen iodide, iodine, alkali metal iodides, alkaline earth metal iodides, organic iodides, or any other source which will provide hydrogen iodide under hydrocarboxylation conditions. Preferred sources of iodide include hydrogen iodide, acetyl iodide, 4-iodobutyl acetate, aryl iodides, $C_1$–$C_{10}$ alkyl iodides, such as methyl iodide, iodoethane, 1-iodopropane, 2-iodopropane, 1,4-diiodobutane, and iodopentane. The iodide and iridium can be present in the same compound, e.g., as in iridium(III) iodide. The most preferred sources of iodide promoter are hydrogen iodide, aqueous hydrogen iodide, methyl iodide, and iodobutanes.

In the synthesis of adipic acid by the present process, about a molar equivalent of water based on the pentenoic acid or ester compound is necessary for high conversion; therefore at least about a stoichiometric amount of water is employed. Although an excess of water may be present in the process of the present invention, large excesses should be avoided. In general, the concentration of water at the start of the hydrocarboxylation reaction should be no more than about 15% by weight of the total reaction mixture. In order to obtain higher reaction rates and better product linearity, it is preferred that the concentration of water at the start of the hydrocarboxylation reaction be no more than about 10% by weight.

Adipic acid synthesis reaction temperatures in the range of 100° to 220° C. may be employed in the practice of this invention. However, at lower temperatures, the reaction rates are slower and the linear selectivity is somewhat less, while at temperatures above 220° C., significant decomposition of the product adipic acid can occur. In general temperatures in the range of 130° to 220° C. are satisfactory, while 170° to 210° C. are preferred.

In the synthesis of adipic acid although higher pressures may be used, total pressures in the range of about 0 to 2000 pounds per square inch (psig) are the most conveniently employed in the process of this invention.

In a continuous process according to the present invention, the dehydrocarboxylation is preferably run at a temperature of 190° to 230° C. and at a pressure of 40 to 1500 mm of mercury. These conditions are also preferred for the simultaneous distillation that produces the recycle stream of pentenoic acid isomers.

EXAMPLES

Example 1

A 100 ml zirconium mechanically stirred autoclave was flushed with carbon monoxide. It was then charged with 87 g of a solution containing 40 grams (273 mmole) of 2-methylglutaric acid (MGA), 0.40 grams 57% aqueous HI (1.8 mmole HI), 0.31 grams (0.89 mmole) Ir(CO) 2(acac), 0.53 grams (29 mmoles) water, 0.31 grams (3.2 mmoles) phosphoric acid, 40 grams (400 mmoles) gamma valerolactone, 4.2 grams (42 mmoles) t-3-pentenoic acid, and 0.1 grams (1 mmole) 4-pentenoic acid. The autoclave was pressured with CO to 10 psi and then heated to 180° C. The autoclave pressure was then immediately adjusted to 400 psi with CO. After the reaction was allowed to run for a total of 5 hours, it was cooled to 50° C., vented, and the product was discharged. The autoclave was washed first with 80 ml of 0.1% HI in acetic acid at 200° C., then with 80 ml of acetone at 20° C., and finally with 80 ml of acetic acid at 20° C. The first wash was included with the reaction product for analysis. Subsequent washes were discarded.

Three samples each of the feed mixture and the product were esterified by heating in a sealed vial at 90° C. for 1 hour with BF3/methanol esterification catalyst so that the components could be measured by capillary gas chromatography as the methyl esters. The analysis is shown in Table 1.

TABLE 1

| REACTION PRODUCTS VS FEEDS | | |
|---|---|---|
| | Average Mole % of Feed | Average Mole % of Product |
| 3-Pentenoic Acid | 4.678 | 0.935 |
| 2-Pentenoic Acid | 0.935 | 0.847 |
| 4-Pentenoic Acid | 0.129 | 0.032 |
| Adipic Acid | 0.006 | 2.630 |
| Valerolactone | 59.734 | 60.561 |
| Valeric/2-Methylbutyric Acid | 0 | 0.538 |
| 2-Ethylsuccinic Acid | 0 | 0.225 |
| 2-Methylglutaric Acid | 34.479 | 34.206 |

Fraction of final products recovered as adipic acid = 83%

Example 2

This Example illustrates the recovery of crude adipic acid from the process of the present invention when the concentration of valerolactone in the reaction mixture was 30% by weight. The hydrocarboxylation reaction was carried out as described in Example 1 except the concentration of valerolactone in the reaction mixture was 30% by weight. A 500 gram sample of the product stream was placed in a 1-liter glass crystallizer equipped with magnetic stirring and a total reflux condenser (20° C.).

This product stream mixture consisting of (by weight):

30% gamma-Valerolactone
25% Adipic Acid
32% 2-Methyl Glutaric Acid
5% Tiglic Acid
3% Valeric Acid
3% 2-Methyl Butyric Acid
1% Caproic acid
1% 3-Pentenoic Acid The crystallizer contents were heated up above 95° C. to dissolve all solids and produce a homogeneous solution. The solution was then cooled down under stirring to 40° C. over a 2 hour period to yield a slurry of adipic acid crystals.

80 ml. of the product slurry was vacuum filtered in a glass-fritted funnel to separate the adipic acid crystals from the liquid filtrate. These crystals were then washed three times with 15 ml. volumes of valerolactone to yield 16 g. of adipic acid crystals.

The adipic acid crystals were analyzed by for impurities by gas phase chromatography. The concentrations of monobasic acid impurities co-crystallized in the adipic acid crystals were 265 ppm valeric acid and 565 ppm caproic acid.

The ease at which the adipic acid crystals were separated from the liquid filtrate is measured by the intrinsic permeability, K, defined as: $K = Q*L/A/P$ where Q is the flowrate of liquid filtrate through a crystal bed of thickness, L, and cross-sectional area, A, under pressure drop P. The higher the value of the intrinsic permeability, the more easily the crystals are to filter.

The intrinsic permeability of the adipic acid crystals formed in example 1 was 63 cm2/atm-min.

Example 3

This Example illustrates the recovery of crude adipic acid from the process of the present invention when the concentration of valerolactone in the reaction mixture was 50% by weight. The hydrocarboxylation reaction was carried out as described in Example 1 except the concentration of valerolactone in the reaction mixture was 50% by weight. A 500 gram sample of the product stream was placed in a 1-liter glass crystallizer equipped with magnetic stirring and a total reflux condenser (20° C.) This product stream mixture consisting of (by weight):

50% gamma-Valerolactone
25% Adipic Acid
16% 2-Methyl Glutaric Acid
2.6% Tiglic Acid
3.5% Valeric Acid
1.3% 2-Methyl Butyric Acid
1% Caproic acid
0.6% 3-Pentenoic Acid The concentrations of monobasic acid impurities co-crystallized in the adipic acid crystals are 127 ppm valeric acid and 215 ppm caproic acid. The intrinsic permeability of the adipic crystals formed in example 2 is 393 cm2/atm-min.

Example 4

This Example illustrates the recovery of crude adipic acid from the process of the present invention when the concentration of valerolactone in the reaction mixture was 60% by weight. The hydrocarboxylation reaction was carried out as described in Example 1 except the concentration of valerolactone in the reaction mixture was 60% by weight. A 500 gram sample of the product stream was placed in a 1-liter glass crystallizer equipped with magnetic stirring and a total reflux condenser (20° C.). This product stream mixture consisting of (by weight):

60% gamma-Valerolactone
23% Adipic Acid
10.3% 2-Methyl Glutaric Acid
1.6% Tiglic Acid
3% Valetic Acid
0.8% 2-Methyl Butyric Acid
1% Caproic acid
0.3% 3-Pentenoic Acid The concentrations of monobasic acid impurities co-crystallized in the crystals are 107 ppm valetic acid and 275 ppm caproic acid.

The intrinsic permeability of the adipic crystals formed in example 3 is 510 cm2/atm-min.

Comparative Example 2

For comparison the product adipic acid was crystallized from a product mixture typical of that of the prior art.

Example 2 is reproduced except the simulated product stream sample consists of (by weight):

3% gamma-Valerolactone
20% Adipic Acid
28% 2-Methyl Glutaric Acid
14% Ethyl Succinic Acid
10% Dimethyl Succinic Acid
10% Valeric Acid
10% 2-Methyl Burytic Acid
1% 3-Pentenoic Acid
4% Water The concentration of valeric acid impurity co-crystallized in the adipic acid crystals is 9521 ppm.

The intrinsic permeability of the adipic crystals formed in example 4 is 8 cm2/atm-min.

We claim:

1. A process for the preparation of adipic acid from pentenoic acid or mixtures of pentenoic acid isomers which comprises:

(a) forming a reaction mixture containing the pentenoic acids or mixtures thereof, water, carbon monoxide, gamma-valerolactone, an iridium catalyst promoted with bromide or iodide and optionally a strong acid reaction promoter wherein the concentration of gamma-valerolactone is from 30 to 70% by weight of the reaction mixture; and (b) reacting the mixture to convert pentenoic acid to adipic acid and branched six carbon dicarboxylic isomers of adipic acid.

2. The process of claim 1 wherein the strong acid promoter is selected from the group consisting of triflic, p-toluenesulfonic and phosphoric acid.

3. The process of claim 1 wherein the concentration of gamma-valerolactone is from 50 to 70% by weight of the reaction mixture.

4. The process of claim 1 further comprising subsequent to step (b), the steps:

(c) removing a portion of the mixture as a product stream and recovering crude adipic acid and forming a by-product stream;

(d) subjecting the by-product stream to dehydrocarboxylation to convert a part of the by-product branched six carbon dicarboxylic isomers of adipic acid to pentenoic acid isomers forming a recycle stream; and (e) combining the recycle stream and fresh feed to form the reaction mixture of step (a).

5. The process of claims 1 or 4 wherein all or a part of the pentenoic acid or pentenoic acid isomers feed is a pentenoic acid monoester and wherein the product adipic acid monoester formed therefrom is hydrolyzed to form adipic acid.

* * * * *